(12) United States Patent
Albitar (10) Patent No.: US 10,227,657 B2
(45) Date of Patent: Mar. 12, 2019

(54) METHOD FOR HIGH SENSITIVITY DETECTION OF MYD88 MUTATIONS

(71) Applicant: Neogenomics Laboratories, Inc., Fort Myers, FL (US)

(72) Inventor: Maher Albitar, Valley Center, CA (US)

(73) Assignee: NEOGENOMICS LABORATORIES, INC., Fort Myers, FL (US)

( * ) Notice: Subject to any disclaimer, the term of this patent is extended or adjusted under 35 U.S.C. 154(b) by 0 days.

(21) Appl. No.: 15/201,302

(22) Filed: Jul. 1, 2016

(65) Prior Publication Data

US 2017/0002427 A1 Jan. 5, 2017

Related U.S. Application Data (60) Provisional application No. 62/187,735, filed on Jul. 1, 2015.

(51) Int. Cl.
 *C12Q 1/68* (2018.01)
 *C12Q 1/6886* (2018.01)
(52) U.S. Cl.
 CPC ..... *C12Q 1/6886* (2013.01); *C12Q 2600/154* (2013.01); *C12Q 2600/156* (2013.01)
(58) Field of Classification Search
 None
 See application file for complete search history.

(56) References Cited

U.S. PATENT DOCUMENTS

| 9,944,991 | B2 | 4/2018 | Ghobrial et al. |
| 2010/0009355 | A1 | 1/2010 | Kolodney |
| 2014/0249142 | A1 | 9/2014 | Treon |
| 2017/0051357 | A1 | 2/2017 | Albitar |

FOREIGN PATENT DOCUMENTS

| EP | 2774997 A1 | 9/2014 |
| WO | 1996017945 A1 | 6/1996 |
| WO | 2007100911 A2 | 9/2007 |
| WO | 2013123031 A2 | 8/2013 |
| WO | 2014018567 A1 | 1/2014 |
| WO | 2015085075 A1 | 6/2015 |

OTHER PUBLICATIONS

Albitar, A. et al., High Sensitivity testing Shows Multiclonal Mutations in Patients with CLL Treated with BTK Inhibitor and Lack of Mutations in Ibrutinib-Naive Patients, Blood, Dec. 3, 2015, 126:716.
Dominguez, PL et al., Wild-Type Blocking Polymerase Chain Reaction for Detection of Single Nucleotide Minority Mutations from Clinical Specimens, Oncogene, Aug. 22, 2005, vol. 24(45), pp. 6830-6834.
Honigberg, Lee A. et. al.; The Bruton tyrosine kinase inhibitor PCI-32765 blocks B-cell activation and is efficacious in models of autoimmune disease and B-cell malignancy; PNAS, Jul. 20, 2010 vol. 107, No. 29, pp. 13075-13080.
Huang, MMC et al., Highly Sensitive KRAS Mutation Detection from Formalin-Fixed Paraffin-Embedded Biopsies and Circulating Tumour Cells Using Wild-Type Blocking Polymerase Chain Reaction and Sanger Sequencing; Molecular Diagnosis & Therapy, Aug. 2014, vol. 18, No. 4, pp. 459-468.
PCT/US2016/047404, International Search Report and Written Opinion, dated Dec. 7, 2016, 9 pgs.
Albitar, A. et al., "Positive Selection and High Sensitivity Test for MYD88 Mutations Using Locked Nucleic Acid," International Journal of Laboratory Hematology, Jan. 21, 2016, vol. 38, pp. 133-140.
Capaldi, IB et al., "Detection of MYD88 L265P Mutations in Formalin-Fixed and Decalcified BM Biopsies from Patients with Lymphoplasmacytic Lymphoma," Experimental and Molecular Pathology, May 16, 2014, vol. 97, pp. 57-65.
Do, H. et al., "Dramatic Reduction of Sequence Artefacts from DNA Isolated from Formalin-Fixed Cancer Biopsies by Treatment with the Uracil-DNA Glycosylase," Oncotarget, May 24, 2012, vol. 3, pp. 546-558.
International Search Report for PCT/US2016/04869, dated Oct. 5, 2016, 3 pages.
Written Opinion for PCT/US2016/040869, dated Oct. 5, 2016, 5 pages.
Loiarro, M, at al.,"Identification of critical residues of the MyD88 death domain involved in the recruitment of downstream kinases", J Biol Chem 2009, 284(41): 28093-28103.
Treon, SP, et al., "MYD88 L265P somatic mutation in Waldenström's macroglobulinemia.", N Engl J Med 2012, 367(9): 826-833.
Ngo, VN, et al., "Oncogenically active MYD88 mutations in human lymphoma", Nature 2011, 470(7332): 115-119.
Varettoni, M, et al., "Prevalence and clinical significance of the MYD88 (L265P) somatic mutation in Waldenström's macroglobulinemia and related lymphoid neoplasms", Blood 2013, 121(13): 2522-2528.
Salar, A., et al., 1690 MYD88 (L265P) Mutation Confers Very Poor Response and Outcome after Second-Line Therapy in Patients with Diffuse Large B-Cell Lymphoma (DLBCL), Presentation at 56th American Society of Hematology Meeting and Exposition, San Francisco, CA, 2014.
Pasqualucci, L., et al., "Analysis of the coding genome of diffuse large B-cell lymphoma," Nat Genet 2011, 43(9): 830-837.
Wang, D, et al., "508 Novel Approach to the Potential Treatment of Patients with B-Cell Lymphomas Harboring the MYD88 L265P Mutation: Combination Treatment with TLR Antagonist and Rituximab", Presentation at 56th American Society of Hematology Meeting and Exposition, San Francisco, CA, 2014.

(Continued)

*Primary Examiner* — Katherine D Salmon
(74) *Attorney, Agent, or Firm* — Eleanor Musick; Musick Davison LLP (57) ABSTRACT

A method for increasing sensitivity for detecting minority mutations in MYD88 uses a locked nucleic acid oligo to block amplification of wild-type DNA in DNA isolated from patient FFPE tissue, bone marrow aspirate or peripheral blood samples during PCR while still allowing sequencing and visualization of the PCR product. Further improvement to the sensitivity may be achieved by using a uracil DNA-glycosylase treatment to remove sequence artifacts commonly found in formalin-fixed, paraffin-embedded tissue.

9 Claims, 7 Drawing Sheets

Specification includes a Sequence Listing.

(56) References Cited

OTHER PUBLICATIONS

Xu L, et al., "MYD88 L265P in Waldenström macroglobulinemia, immunoglobulin M monoclonal gammopathy, and other B-cell lymphoproliferative disorders using conventional and quantitative allele-specific polymerase chain reaction", Blood 2013, 121(11): 2051-2058.

Dominguez, PL, et al., "Wild-type blocking polymerase chain reaction for detection of single nucleotide minority mutations from clinical specimens," Oncogene 2005, 24(45), 6830-6834.

Gallegos-Ruiz, MI, et al., "EGFR and K-ras mutation analysis in non-small cell lung cancer: comparison of paraffin embedded versus frozen specimens," Cell Oncol 2007, 29(3): 257-264.

Yost, SE, et al, "Identification of high-confidence somatic mutations in whole genome sequence of formalin-fixed breast cancer specimens," Nucleic Acids Res 2012, 40 (14).

Do, H, et al., "Reducing sequence artifacts in amplicon-based massively parallel sequencing of formalin-fixed paraffin-embedded DNA by enzymatic depletion of uracil-containing templates," Clin Chem 2013, 59(9), 1376-1383.

Adams, RLP, et al., "Increased G+C content of DNA stabilises methyl CpG dinucieotides," Nucl Acids Res 1984, 12(14): 5869-5877.

Adams, RL, et al., "CpG deficiency, dinucleotide distributions and nucleosome positioning," Eur Biochem 1987, 165(1): 107-115.

Troen, G, et al, CD79B and MYD88 Mutations in Splenic Marginal Zone Lymphoma. ISRN Oncology, 2013, 252318.

Huang, Qing, et al.; "High sensitive mutation analysis on KRAS gene using LNA/DNA chimeras as PR amplification blockers of wild-type alleles", Molecular and Cellular Probes 24 (2010) pp. 376-380.

Liu, Ta-Ming, et al.; Hypermorphic mutation of phospholipase C, $\gamma 2$ acquired in ibrutinib-resistant CLL confers BTK independency upon B-cell receptor activation:; Blood; Jul 2, 2015; 126: pp. 61-68; Epub May 13, 2015.

Shendure, Jay, et al. "Next-generation DNA sequencing", Nature Biotechnology, Oct. 26, 2008, (10): 1135-45.

Woyach, Jennifer A. et al.; "Resistance Mechanisms for the Bruton's Tyrosine Kinase Inhibitor Ibrutinib"; The New England Journal of Medicine, Jun. 12, 2014, pp. 2286-2294, 370:24.

Woyach, Jennifer A. et al.; "Supplement to: Resistance Mechanisms for the Bruton's Tyrosine Kinase Inhibitor Ibrutinib"; Jun. 12, 2014, pp. 2286-2294, 370:24;The New England Journal of Medicine, 2014, 42 pages.

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
tgtaaaacga cggccagt                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
caggaaacag ctatgacc                                                 18

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tgccaggggt acttagatgg                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ggttggtgta gtcgcagaca                                               20

<210> SEQ ID NO 5
<211> LENGTH: 17
<212> TYPE: DNA
<213> ORGANISM: Artificial Sequence
<220> FEATURE:
<221> NAME/KEY: oligomeric compound
<223> OTHER INFORMATION: MYD88 LNA (TCAGA+AG+C+G+A+C+T+G+A+T+CC/invdT/)
<220> FEATURE:
<221> NAME/KEY: misc_feature
<222> LOCATION: 6, 9, 11, 13, 15, 17, 19, 21, 23, 25
<223> OTHER INFORMATION: locked nucleotide
```

```
<220> FEATURE:
<221> NAME/KEY: misc_feature
<222> LOCATION: 17
<223> OTHER INFORMATION: 3' inverted dT

<400> SEQUENCE: 5
tcagcagcga ctgatcc                                                      17
```

METHOD FOR HIGH SENSITIVITY DETECTION OF MYD88 MUTATIONS

RELATED APPLICATIONS

This application claims the benefit of the priority of U.S. Provisional Application No. 62/187,735, filed Jul. 1, 2015, which is incorporated herein by reference in its entirety.

FIELD OF THE INVENTION

The present invention relates to a method for increasing detection sensitivity for minority mutations in MYD88.

BACKGROUND OF THE INVENTION

All cancers are believed to be due to mutations. Testing for myeloid differentiation primary response gene 88 (MYD88) has significant therapeutic and diagnostic value in a range of cancer types, including Waldenström's Macroglobulinemia (WM), diffuse large B-Cell lymphoma (DLBCL), monoclonal gammopathy of unknown significance (MGUS), and splenic marginal zone lymphoma (SMZL), collectively, "MYD88-associated cancers". MYD88 is an adaptor molecule in a toll-like receptor and interleukin-1 receptor signaling pathway. Mutation in MYD88 results in over-activation of toll-interleukin-receptor pathways, subsequent phosphorylation of IRAK1/4, and release of nuclear factor-kappa-B (NF-κB) drive cell survival and proliferation. It has been demonstrated in DLBCL and WM that inhibition of MYD88 signaling results in decreased NF-κB activity and reduced cell survival. MYD88 mutations are also associated with greater disease burden in patients with DLBCL and poor overall survival following initial and secondary therapy options. MYD88 mutations are detected in 39% of activated B-cell-like (ABC) DLBCL. These mutations are, however, rarely discovered in germinal center B-cell-like (GCB) DLBCL and primary medastinal B-cell lymphoma (PMBL). Therefore, MYD88 mutation status may serve as a surrogate marker for the ABC-subtype. Recent work on ABC-DLBCL and WM has demonstrated increased response to therapy—in both disease types—by combination therapy with a toll-like receptor agonist (IMO-8400) and Rituximab in mouse models. As such, MYD88 mutation status is a useful marker in determining prognosis and in guiding current and future therapy options.

MYD88 mutations are found in almost all cases of WM and ~50% of patients with Immunoglobulin M (IgM)-secreting MGUS, while these mutations are rarely detected in patients with SMZL (0-6%) and are absent in multiple myeloma (0%). Differential diagnosis of WM from SMZL and IgM-multiple myeloma is often difficult because of overlapping morphologic, immunophenotypic, cytogenetic, and clinical characteristics. MYD88 is, therefore, a useful marker for accurate diagnosis given its positive mutation status presenting primarily in WM. MYD88's diagnostic, prognostic, and therapeutic power necessitates the development of high-throughput, high-sensitivity assays.

Most mutations in MYD88 occur at codon L265, converting leucine to proline (L265P); however, mutations at M232, P258, L103, and Q143 have also been reported. Allele-specific (AS) polymerase chain reaction (PCR) based assays have been developed for MYD88 L265P and demonstrated the ability to detect minute fractions of L265P positive cells. However, inherent limitations in this methodology prohibit AS-PCR from detecting variants other than those previously described or specifically designed for this purpose. Thus, the need for an alternative methodology that can be used in routine lab work at larger volumes is desired.

Wild-type blocking PCR (WTB-PCR) using locked nucleic acid (LNA) has demonstrated high sensitivity and versatility in the detection of low percentage mutant populations. By adding an LNA oligo (10-12 NT), complementary to the region of the hotspot, amplification of the WT allele is inhibited, leading to experimentally driven positive selection for mutant alleles. This is accomplished by designing the LNA oligo so that it anneals to the template strand during the primer annealing step of PCR and melts from mutant template DNA—but not WT DNA—during extension. Because a single nucleotide mismatch in the LNA-DNA hybrid greatly decreases its melting temperature, only mutant template DNA is free to complete its extension. Therefore, WT DNA is amplified linearly but mutant DNA is amplified exponentially. Traditional Sanger sequencing can then be performed.

Sanger sequencing has traditionally been the gold standard in testing for both known and unknown somatic mutations. One of the limitations of Sanger sequencing is its limit of detection (~10-20% mutant allele in a background of WT). This level of sensitivity is inappropriate for detecting low level somatic mutations that may be present in samples from premalignant tissues or patients with few circulating tumor cells, or when bone marrow (BM) is patchy. This also makes assessing residual disease after therapy or detecting emerging resistance mutations during therapy difficult by conventional sequencing alone. By replacing conventional PCR with LNA-mediated wild-type blocking PCR (WTB-PCR) in Sanger sequencing, sensitivities of up to 0.1% mutant allele in a background of WT can be achieved. In WTB-PCR enrichment for mutant alleles is achieved via the addition of a short (~10-14 NT) LNA oligonucleotide that binds preferentially to WT DNA thereby preventing amplification of WT DNA. The mutant enriched WTB-PCR product can then be sequenced. By blocking WT DNA rather than selecting for specific mutations WTB-PCR allows for enrichment of both known and unknown mutations present in minute cell fractions.

Among the most prevalent methods for detecting mutations in small cell fractions are allele-specific PCR (AS-PCR) and real-time quantitative PCR (qPCR). Both are limited by false-positives and the ability to only detect one mutation for which the assay was designed. WTB-PCR, however, allows the user to visualize sequencing traces, which enables the detection of multiple mutation types and can aid in ruling out false positives due to artifacts or deamination events. Next-generation sequencing (NGS) may offer a suitable alternative to conventional sequencing, however, substantially greater costs, complexity, and longer assay time render it an unnecessary option for many disease types with few distinct molecular markers or for monitoring patients on therapy for emerging resistance mutations. Furthermore, high false positive rate when detecting variants with mutant allele frequencies of less than 5% can pose a problem for amplicon-based NGS.

The utility of WTB-PCR over AS-PCR lies in its ability to block WT allele amplification rather than amplifying one specific variant allele. In addition, these variant alleles can then be visualized and confirmed via sequencing—contrary to AS-PCR—thereby avoiding false positives. This enrichment of the mutant DNA is particularly useful in testing clinical samples that may contain relatively few neoplastic cells. DLBCL or WM cells may constitute a small percent-

BRIEF SUMMARY OF THE INVENTION

According to an embodiment of the invention, a method is provided for detecting suspected WM or other diseases associated with MYD88 mutation using LNA-augmented PCR, followed by bi-directional Sanger sequencing.

In an exemplary embodiment, a method is provided for increasing sensitivity for detecting minority mutations in MYD88 when compared to traditional PCR followed by Sanger sequencing (1 mutant allele in a background of 200 WT alleles). The methodology uses a locked nucleic acid oligo to block amplification of wild-type DNA during PCR while still allowing sequencing and visualization of the PCR product, giving it advantages over other methodologies such as allele-specific PCR. While the exemplary embodiments employ Sanger sequencing, it will be readily apparent to those in the art that other sequencing techniques may be used, including, but not limited to next generation sequencing (NGS), polymerase chain reaction (PCR), pyrosequencing, dye sequencing, sequencing by synthesis, and ion semiconductor sequencing, among others.

In some embodiments, an uracil DNA-glycosylase treatment may be used to remove sequence artifacts commonly found in formalin-fixed, paraffin-embedded tissue. The inventive method provides significant improvement in sensitivity when compared to traditional PCR, which failed to detect MYD88 mutations in 65% of the samples that were clearly positive by the inventive approach using wild-type blocking PCR. While LNA is used for blocking in the exemplary embodiments, the same is applicable for other synthetic nucleotides such as BNA, PNA, or XNA.

In one aspect of the invention, a method for screening and/or monitoring a patient for MYD88 mutations includes the steps of isolating DNA from a sampling bone marrow aspirate (BM), fresh peripheral blood (PB), and formalin-fixed, paraffin-embedded (FFPE) tissues sample obtained from the patient suspected of having a condition associated with MYD88 mutations; performing PCR on the extracted DNA to produce amplified DNA while blocking amplification of wild-type DNA; sequencing the amplified DNA in an automated sequencer; analyzing an output of the automated sequencer to identify mutations in the sequence. In one embodiment, the amplification of wild-type DNA is blocked by a LNA oligo. The LNA oligo may have the sequence TCAGA+AG+C+G+A+C+T+G+A+T+CC/invdT (SEQ ID NO. 5), which covers amino acids Q262-I266. The LNA oligo may further be a 17mer with 10 LNA bases that are denoted as "+N" and wherein the remaining 7 bases are ordinary DNA nucleotides. In certain embodiments, the method may further include, prior to sequencing, applying a uracil DNA-glycosylase treatment to the sample to remove sequence artifacts.

Further embodiments include a kit for diagnosing, monitoring and managing a patient with a MYD88-associated cancer. This kit includes a primer with SEQ ID NO. 1, a primer with SEQ ID NO. 2 and a LNA oligo with SEQ ID NO. 5. The kit is suitable for diagnosing, monitoring and managing a patient suffering from an MYD88-associated cancer including any of the following diseases: Waldenström's Macroglobulinemia (WM), diffuse large B-Cell lymphoma (DLBCL), monoclonal gammopathy of unknown significance (MGUS), and splenic marginal zone lymphoma (SMZL).

DETAILED DESCRIPTION OF EXEMPLARY EMBODIMENTS

The following description details the procedures and results for the inventive method for increasing sensitivity for detecting minority mutations in MYD88. In an exemplary embodiment, the methodology uses a locked nucleic acid (LNA) oligo to block amplification of wild-type DNA during PCR while still allowing sequencing and visualization of the PCR product, giving it advantages over other methodologies such as allele-specific PCR. In one embodiment, a uracil DNA-glycosylase treatment may be used to remove sequence artifacts commonly found in formalin-fixed, paraffin-embedded tissue. Results from analysis of randomly selected 37 MYD88 mutated, clinically tested samples demonstrate that traditional PCR failed to detect MYD88 mutations in 65% of the samples that were clearly positive by wild-type blocking PCR. Thus, this methodology is essential for attaining accurate results in clinical testing. While the exemplary embodiment uses LNA for blocking, the inventive method may also employ other synthetic nucleotides for blocking amplification of wild-type DNA and/or enhancing amplification of the mutant allele. Such alternatives include BNA (bridged nucleic acids), PNA (peptide nucleic acids), or XNA (xeno nucleic acids).

Figure 1:
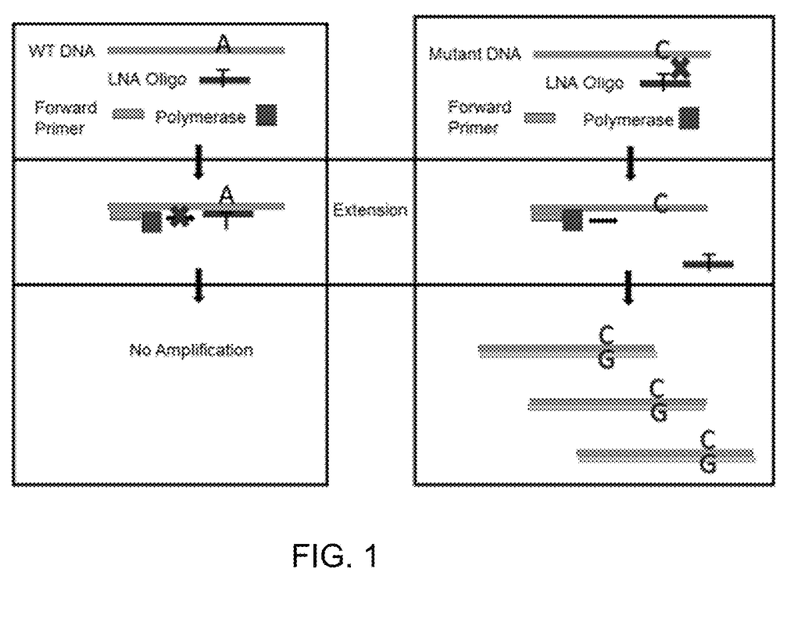
FIG. 1 is a diagrammatic overview of WTB-PCR. A single nucleotide mismatch in the LNA-DNA hybrid decreases $T_m$ by up to 30° C. By designing the LNA oligonucleotide to have a $T_m$ of 10-15° C. above the temperature during extension, amplification of WT DNA is blocked while allowing amplification of mutant DNA.

A conceptual overview of WTB-PCR during extension is presented in FIG. 1. Because a single nucleotide mismatch in the LNA-DNA hybrid greatly decreases its melting temperature ($\Delta T_m$=20-30° C.), amplification of the WT allele is blocked, while mutant template DNA is free to complete extension. In this manner, mutant DNA is amplified exponentially while WT DNA is amplified only linearly.

Figure 2:
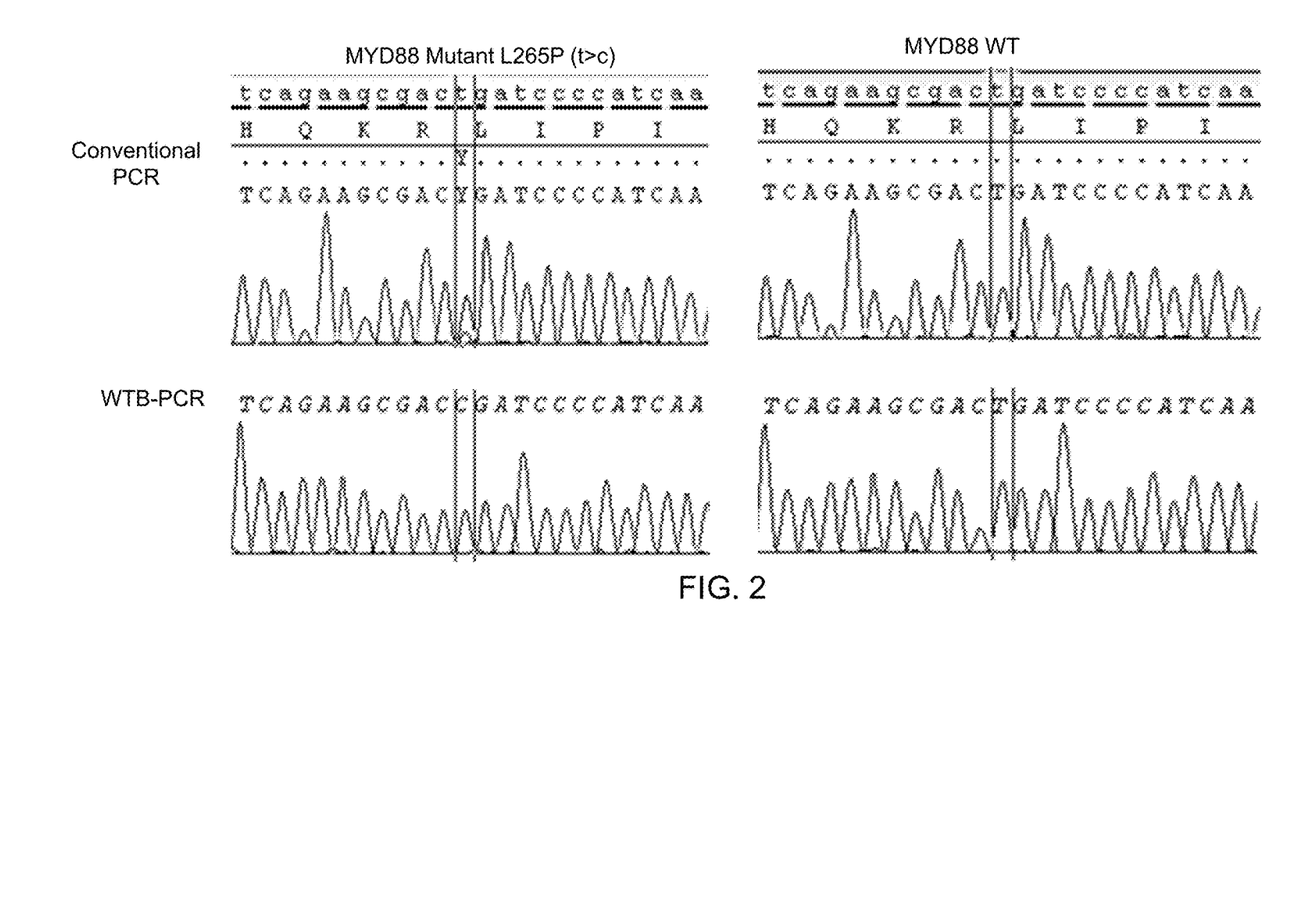
FIG. 2 illustrates test results for genomic DNA from patients with and without mutations comparing conventional and WTB-PCR, demonstrating the typical enrichment achievable by WTB-PCR. The final concentration of LNA used to achieve WTB-PCR was selected in order to achieve maximum mutant enrichment while not causing false positives in WT DNA or blocking amplification of WT DNA entirely.

A demonstration of the mutant enrichment achieved by WTB-PCR is presented in FIG. 2. Genomic DNA from patients with and without mutations were tested by both conventional and WTB-PCR and then sequenced to demonstrate the typical enrichment achievable by WTB-PCR and a lack of false positives in WT DNA. The working concentration of LNA used in WTB-PCR MMX should be determined by titration experiments and should achieve the desired level of mutant enrichment while not resulting in false positives or blocking amplification of WT DNA entirely. Sequencing analysis of WTB-PCR product demonstrates enrichment for the mutant allele and a limit of detection in excess of 0.5% mutant allele in a background of WT compared with 16% in conventional PCR.

The effects of this increase in sensitivity in clinical testing may vary depending on the amount of neoplastic cells in the samples tested. In a methods comparison study, the WTB-PCR assay described here has demonstrated that 64% of MYD88 mutations would be missed by conventional testing of patients with WM or MGUS.

The WTB-PCR assay disclosed herein uses a generic set of primers with a LNA oligo designed to block amplification of WT DNA during extension (FIG. 1). The WTB-PCR product is then sequenced for mutational analysis. The utility of WTB-PCR/Sanger lies in its simplicity, high-sensitivity, and high-throughput. Using the techniques described herein, most existing Sanger based assays can be simply modified via the addition of a blocking LNA oligonucleotide to greatly increase sensitivity. In the example assays described below, the addition of a single LNA oligonucleotide to PCR increased the limit of detection from approximately 16% mutant allele in a background of WT for the conventional assay to >0.5% in the WTB-PCR assay. The effect of which is a 64% reduction in false negatives seen in clinical testing. Confirming the presence of mutations in MYD88 has significant diagnostic and prognostic implications; falsely reporting a case as negative may have serious consequences on overall therapy and patient management. Testing with WTB-PCR is therefore of great importance, particularly in patients with relatively low abnormal cellularity. WTB-PCR techniques vary considerably and are sometimes referred to interchangeably with LNA, BNA, or PNA-mediated PCR clamping or PCR-clamp-probe assays. Some variations utilizing WTB-PCR involve a qPCR assay, which necessitates designing an additional fluorescent probe for a specific mutation. A significant challenge associated with this technique includes the need to develop competitively binding probes that accurately discriminate between WT and mutant alleles. Furthermore, because a mutation specific probe is required, the qPCR approach lacks the ability to detect unknown mutations. Another variation of WTB-PCR blocks WT amplification in an allele-specific manner. Instead of using mutation-specific primers however, a LNA probe specific for the WT allele inhibits complete primer binding. While this approach does not require a mutation-specific probe like qPCR, it fails to discriminate between mutations and polymerase induced errors can lead to increased false positives. Exponential amplification of those polymerase induced errors through PCR may obscure the detection of rare mutational events. Any approach that uses PCR amplification to enrich for mutations has its accuracy limited by the frequency of PCR errors. A fundamental advantage of WTB-PCR/Sanger over many other high-sensitivity methodologies is that it prevents amplification of both WT template and mutant template whose mutations occur outside the gene region targeted by LNA oligonucleotide. Using the inventive approach, PCR errors introduced by polymerases are effectively filtered out along with WT DNA. Contrary to AS-PCR or qPCR however, enrichment is retained for unknown mutations that occur within the region covered by the LNA oligo. In the case of MYD88, WTB-PCR allowed the detection of both L265P and R264* mutations. Others have similarly reported the detection of multiple, low-frequency mutations with the use of WTB-PCR. This makes WTB-PCR ideal for both research and clinical purposes.

Along with high sensitivity and inherent internal controls for eliminating false positives, WTB-PCR's flexibility for adapting an existing sequencing assay with very few additional steps with LNA design make it attractive option for many labs with established assays. The same set of PCR primers used in a conventional assay can typically be used in the WTB-PCR variation. Other protocol changes that are highly recommended for WTB-PCR—including UDG treatment of FFPE tissue and appropriate post-PCR purification methodologies—are equally transferable. LNA design, therefore is the critical element in implementing a WTB-PCR assay. Though the procedures disclosed herein represent the most relevant factors in that design, various LNA oligonucleotides should be tested to find one that blocks WT amplification efficiently without secondary effects to PCR. This includes adding or removing LNA bases to adjust $T_m$, shifting the position of the blocking oligo relative to the WT template, and changing the overall length of the oligo. LNA titration experiments should also be employed in order to establish a balance between acceptable occurrences of sequencing artifacts and limit of detection.

Selecting an appropriate methodology for detecting mutations that are present in small cell fractions depends greatly on the application and disease/mutation types. If mutant quantification is desired, qPCR or digital PCR may offer more viable solutions than WTB-PCR/Sanger. Though WTB-PCR is primarily a qualitative assay, it is possible to determine a rough estimate of the mutant allele frequency by testing a sample with conventional and WTB-PCR in parallel. Because the limit of detection for the conventional assay is ~10-20% mutant allele in a background of WT, it is appropriate to conclude that mutations detected by the WTB-PCR assay but not the conventional are present at a concentration less than the limit of detection for the conventional assay. Few assays offer the versatility, simplicity, and robustness of WTB-PCR. The low cost and short turnaround time makes it ideal for assessing residual disease after therapy or monitoring emerging resistance mutations during therapy. Additionally, the ability to detect previously undescribed mutations make WTB-PCR ideal for research purposes.

While the exemplary embodiments described herein employ Sanger sequencing, it will be readily apparent to those in the art that other sequencing techniques may be used, including, but not limited to next generation sequencing (NGS), polymerase chain reaction (PCR), pyrosequencing, dye sequencing, sequencing by synthesis, and ion semiconductor sequencing, among others.

The following examples illustrate use of the inventive method for MYD88 mutation detection.

Example 1: Protocol for MYD88 Assay Using WTB-PCR Testing

DNA Extraction from FFPE Tissue, Peripheral Blood (PB), and Bone Marrow (BM) Aspirate is performed following the steps described below for the appropriate sample type. It should be noted that the procedures described may be specific to a particular manufacturer's/supplier's instructions. Variation to adapt these steps to kits and reagents from other sources will be readily apparent to those of skill in the art.

Tables 1 and 2 below provide reagents and primer sequences, respectively, used in this procedures.

TABLE 1

| Reagent | Vendor | Catalog No. | Description |
|---|---|---|---|
| 100% alcohol | VWR | 89370-084 | Histology grade; 91.5% Ethanol, 5% Isopropyl alcohol, 4.5% Methyl alcohol |
| DNAse, RNAse-free, ultra-pure water | | | |
| Ethanol Absolute | Sigma | E7023 | 200 proof, for molecular biology |
| FastStart Taq DNA polymerase (5 U/ul) | Roche | 12032937001 | With 10X concentrated PCR reaction buffer, with 20 mM MgCl2 |
| Xylene | VWR | 89370-088 | Histology grade |
| BigDye Terminator v3.1 Cycle sequencing kit | Life Technologies | 4337455 | With 5X Sequencing Buffer |
| QIAamp DNA Mini Kit | Qiagen | 51304 | Or equivalent |
| Hi-Di Formamide | ABI | 4311320 | |
| GeneRead DNA FFPE Kit | Qiagen | 180134 | Contains uracil DNA glycosylase necessary for reducing sequencing artifacts |
| Nuclease Free Water | Fischer Scientific | BP2484-100 or equivalent | |
| 2% E-gel 96 Agarose, 8/PK | Invitrogen | Cat#G7008-02 | |
| (3730) POP-7 Polymer | Applied Biosystems | Cat#AB 4335615 | |

TABLE 2

| Primer Name | Vendor | Sequence |
|---|---|---|
| M13-F | Applied Biosystems | 5'-tgt aaa acg acg gcc agt (SEQ ID NO. 1) |
| M13-R | Applied Biosystems | 5'-cag gaa aca gct atg acc (SEQ ID NO. 2) |
| PCR Forward | Integrated DNA Technologies | 5'-tgt aaa acg acg gcc agt TGC CAG GGG TAC TTA GAT GG (SEQ ID NO. 3) |
| PCR Reverse | Integrated DNA Technologies | 5'-cag gaa aca gct atg acc GGT TGG TGT AGT CGC AGA CA (SEQ ID NO. 4) |

For FFPE tissue with GeneRead™ DNA FFPE kit (QIA-GEN®), begin with FFPE tissue from unstained slides (5-10 sections at 5-10 μm thickness). If starting with tissue shavings, use 3-6 sections at 5-10 μm thickness and skip to the instructions from the manufacturer handout included in the kit.

Place the slides in a slide basket and prepare four wash reservoirs—two for xylene (VWR, histology grade) and two for 100% alcohol (VWR histology grade: 91% ethanol, 5% isopropyl alcohol, 4.5% methyl alcohol). The minimum volume of solution that should be added to each basket is 600 ml. Deparaffinize the slides by doing a 5 minute xylene wash in the first tray. Transfer the slides to the second xylene wash reservoir for an additional 5 minutes. After deparaffinization, wash the slides with 100% alcohol for 5 minutes, then transfer the slides to the second alcohol wash reservoir for an additional 5 minutes. Allow the slides to dry completely under a hood before scraping them with a razor blade into a microcentrifuge tube. Note that if an H&E (haematoxylin and eosin) slide with tumor region indicated is available, align the slides and scrape only the tumor region.

After completion of the FFPE tissue preparation steps, proceed with instructions from the manufacturer handout included in kit.

DNA from BM aspirate and Peripheral Blood is extracted using a QIAamp® DNA Mini Kit (QIAGEN®) according to the manufacturer's instructions handout with the following specifications: use 200 μL peripheral blood (PB) or 100 μl BM+100 μl PBS and 4 μl RNase A stock solution. Elute with 100 μl Buffer AE. Eluted DNA is collected in a standard microcentrifuge tube.

DNA Quantification is performed by measuring DNA concentrations using a spectrophotometer ensuring a 260 nm/280 nm ratio of approximately 1.8 (for pure DNA). If the ratio is appreciably lower, it may indicate the presence of protein, phenol, or other contaminants that could interfere with downstream applications. The DNA concentrations may be adjusted to approximately 50-100 ng/μL with appropriate elution buffer.

The design of a primer for wild-type blocking PCR for genes of interest were performed according to previously described general guidelines of PCR primer design. (See, Dieffenbach, C., et al, General concepts for PCR primer design. PCR Methods Appl 3 (3), S30—S37 (1993), incorporated herein by reference.) M13-forward and reverse universal sequencing primers were included in the PCR primers.

The MYD88 assay was developed to amplify exon 5 of MYD88 (G259-N291) and 110 nucleotides located in the 5' intronic region in order to cover the splice site and part of intron 4. The forward and reverse primers were designed with a 5'-M13 sequence (M13-forward: tgt aaa acg acg gcc agt (Applied Biosystems) (SEQ ID NO. 1); M13-reverse: cag gaa aca gct atg acc) (Applied Biosystems) (SEQ ID NO. 2) to allow for annealing of complementary sequencing primers.

For the blocking locked nucleic acid (LNA), guidelines include that the blocking LNA oligonucleotide should be approximately 10-15 bases in length and complementary to the WT template where mutant enrichment is desired. The blocking oligo is designed to have a melting temperature ($T_M$) that is 10-15° C. above the extension temperature during thermocycling. The $T_M$ can be adjusted by adding or removing LNA bases or by substituting LNA bases for DNA. Design considerations to avoid secondary structure formation should also be taken into account. Finally, long stretches (3-4 bases) with LNA G or C bases should be avoided. The $T_M$ Prediction and Oligo Optimizer tools available on the World Wide Web at exiqon.com ("LNA™ Oligo Optimizer" and "LNA Oligo $T_M$ Prediction") provide all necessary data for the design process and are incorporated herein by reference.

The blocking oligonucleotide for MYD88 [MYD88LNA (TCAGA+AG+C+G+A+C+T+G+A+T+CC/invdT/)] (SEQ ID NO. 5) was designed to cover amino acids Q262-I266 and features a 3'-inverted dT to inhibit both extension by DNA polymerase and degradation by 3'-exonuclease. This specific blocking oligo is a 17mer with 10 LNA bases that are denoted as "+N". The remaining 7 bases are ordinary DNA nucleotides.

WTB-PCR setup and thermocycling was performed under the following conditions using a Microcentrifuge Model 5430 (Eppendodorf) and a Mastercycler Pro S Thermocycler (Eppendorf). Space was provided in the PCR plate for inclusion of a positive and negative control (mutant and WT, respectively) and a non-template control to check for contamination.

A WTB-PCR master mix (MMX) was prepared from: 2.5 µl PCR reaction buffer 10×w/20 mM MgCl2, 250 uM dNTPs, 0.2 uM forward and reverse primer, 1.2 uM MYD88LNA, and DNAse, RNAse-free, ultra-pure $H_2O$ to create a final solution volume of 21.75 µl per reaction. It should be noted that the working concentrations are for the final reaction volume of 25 µl (after addition of DNA template and Fast Taq polymerase). Also, note that conventional PCR MMX is prepared by simply omitting the addition of LNA. Otherwise, all protocol steps remain identical for both WTB and conventional PCR. This can be used in validation and determining enrichment achieved by addition of LNA. Next, the MMX was vortexed thoroughly. The MMX can be stored at −80° C. for up to a year.

After adding 0.25 µl Fast Start Taq DNA polymerase per reaction to the MMX, invert to mix. Once the polymerase has been added to the MMX it should be kept on ice. Note that when calculating the amount of MMX to prepare, sufficient MMX should be provided for 3 additional reactions (controls, mentioned above) and at least 1 additional reaction to allow for pipetting error.

Put a new 96 well PCR plate on a cold plate and pipette 22 µl of MMX with polymerase to each reaction well. Add 3 µl genomic DNA (50-100 ng/µl) to each of the wells containing the MMX with polymerase. Seal the plate and centrifuge briefly to ensure the solution reaches the bottom of each well.

The PCR plate is loaded into the thermocycler and processed under the following conditions: Initial denaturation at 95° C. for 6 minutes; 40 cycles of denaturation at 95° C. for 30 sec, primer annealing at 56° C. for 30 sec, and extension at 72° C. for 1 min 20 sec; final extension at 72° C. for 10 min. It should be noted that best practice involves completing the remainder of the protocol in a physically separate area to avoid amplicon contamination in future setups.

To determine whether WTB-PCR was successful, and to confirm a lack of amplification in the non-template control, gel electrophoresis was performed according to known procedures.

Purification of the PCR Product was achieved using by AMPure XP magnetic beads (Beckman Coulter). The AMPure XP beads are removed from 4° C. and brought to room temperature. 10 µl of PCR product is transferred to a new PCR plate. The AMPure XP was vortexed vigorously to fully re-suspend the magnetic particles. 18 µl of AMPure XP is added to each well on the new plate. Pipette mix 10 times and incubate at room temperature for 5 minutes.

Place the plate onto a DynaMag-96 Side Skirted Magnet Plate for 2 minutes to separate beads from solution, then aspirate the supernatant with a multichannel pipette, being careful to avoid the bead pellet. Dispense 150 µl 70% ethanol into each well and incubate at room temperature for at least 30 sec. Aspirate the ethanol with a multichannel pipette and discard tips. Repeat this wash procedure once more.

Using a 20 µl multichannel pipette, aspirate the remaining ethanol from each well and discard tips.

Once wells are dry HO min), remove from the Magnet Plate and add 40 µl of nuclease free water to each well and pipette mix 15 times. Incubate at room temperature for 2 min., then place the plate onto Magnet Plate for 1 min to separate the beads from solution.

Transfer 35 µl of purified product to a new plate. This is purified PCR product is now ready to proceed with bi-directional sequencing or can be stored at −20° C. until needed. Note that when developing a new assay, quantification of purified PCR product may be required. 1-3 ng/µl amplicon DNA is optimal for bi-directional sequencing. If concentration is consistently low, increase the PCR product and AMPure XP proportionally (1:1.8). If the concentration is consistently high, elute with a greater volume of water.

The WTB-PCT product is sequenced using bi-directional sequencing. Note that this protocol is a modified form of the manufacturer's instructions, which has been optimized to use fewer reagents.

Prepare forward and reverse sequencing reaction mixes with 0.25 µl BigDye® Terminator™ v3.1 Ready Reaction mix (Applied Biosystems), 1.88 µl Sequencing Buffer, 1.78 uM M13-F or M13-R sequencing primers and add DNAse and RNAse-free, ultra-pure $H_2O$ to create a final solution volume of 9 µl per reaction. This sequencing reaction mix can be stored at −20° C. for up to a year. Pipette 9 µl the forward sequencing reaction mix into each well of a new 96 well PCR plate for the forward sequencing reaction. Repeat on a separate plate for the reverse sequencing reaction.

Add 1 µl of the purified WTB-PCR product to each well on both the forward and reverse plates, then seal the plate and centrifuge briefly to ensure the solution reaches the bottom of each well.

Load the PCR plate on a thermocycler and process under the following conditions: 96° C. for 1 min; 30 cycles of 96° C. for 10 sec, 50° C. for 5 sec, 60° C. for 4 min; hold at 4° C. until ready for purification.

For purification of the sequencing products, prepare a fresh 1:25 solution of 3M sodium acetate (pH 5.2) and 100% ethanol, and separately prepare a fresh 70% ethanol solution. Add 30 µl of sodium acetate/ethanol solution to each well of both the forward and reverse sequencing plates and pipette mix 5 times. Reseal the plate and incubate in the dark at room temperature for 20 min.

After incubation, centrifuge the plate at 2250×g for 15 min, then remove the plate sealer and invert over a waste container. Note that the plate should be inverted only once to avoid loosening the pellet from the well bottoms. Place the inverted plate on a clean paper towel and centrifuge at 150×g for 1 min.

Add 150 µl 70% ethanol to each well, then reseal the plate and spin at 2250×g for 5 min. Repeat the steps of inverting the plate then placing it on a clean paper towel. If the wells are not completely dry, they should be allowed to air dry at room temperature to make sure the samples are protected from light while drying.

Once the wells are dry, add 10 μl HI-DI Formamide to each well and pipette mix 10 times, then reseal the plate and place it in the thermocycler. The samples are denatured on the thermocycler at 95° C. for 3 min followed by 4° C. for 5 min.

After denaturing, the plate sealer is replaced with a septa and sequencing is performed using an ABI 3730XL (Applied Biosystems) or equivalent sequencing platform. It should be noted that this protocol is optimized with the 3730XL sequencer and POP-7 Polymer with ABI running buffer 10× with EDTA. This same approach can be used on nearly any sequencer provided the machine being used has been calibrated to use the BigDye terminator v3.1 chemistry.

Analysis of Sequencing Results

Visualization of sequencing traces can be accomplished with a number of commercially-available programs. In the exemplary embodiment, ABI SeqScape v3.0 (Applied Biosystems) was used. The sequences are aligned to MYD88 (NCBI Reference Sequence NM_002468 (*Homo sapiens* myeloid differentiation primary response 88 (MYD88) transcript variant 2, mRNA.) Additional information about this RefSeq is publicly available on the World Wide Web from the National Center for Biotechnology Information (ncbi.nlm.nih.gov), which is incorporated herein by reference.

A conceptual overview of WTB-PCR during extension is provided in FIG. 1. Because a single nucleotide mismatch in the LNA-DNA hybrid greatly decreases its melting temperature ($\Delta T_M$=20-30° C.) amplification of the WT allele is blocked while mutant template DNA is free to complete extension. In this manner, mutant DNA is amplified exponentially while WT DNA is amplified linearly.

A demonstration of the mutant enrichment achieved by WTB-PCR is provided in FIG. 2. Genomic DNA from patients with and without mutations were tested by both conventional and WTB-PCR and then sequenced to demonstrate the typical enrichment achievable by WTB-PCR and a lack of false positives in WT DNA. The working concentration of LNA used in WTB-PCR MMX should be determined by titration experiments and should achieve the desired level of mutant enrichment while not resulting in false positives or blocking amplification of WT DNA entirely. Sequencing analysis of WTB-PCR product demonstrates enrichment for the mutant allele and a limit of detection in excess of 0.5% mutant allele in a background of WT compared with 16% in conventional PCR[3].

The effects of this increase in sensitivity in clinical testing may vary depending on the amount of neoplastic cells in the samples tested. In a methods comparison study, the WTB-PCR assay described here has demonstrated that 64% of MYD88 mutations would be missed by conventional testing of patients with WM or MGUS.

Figure 3:
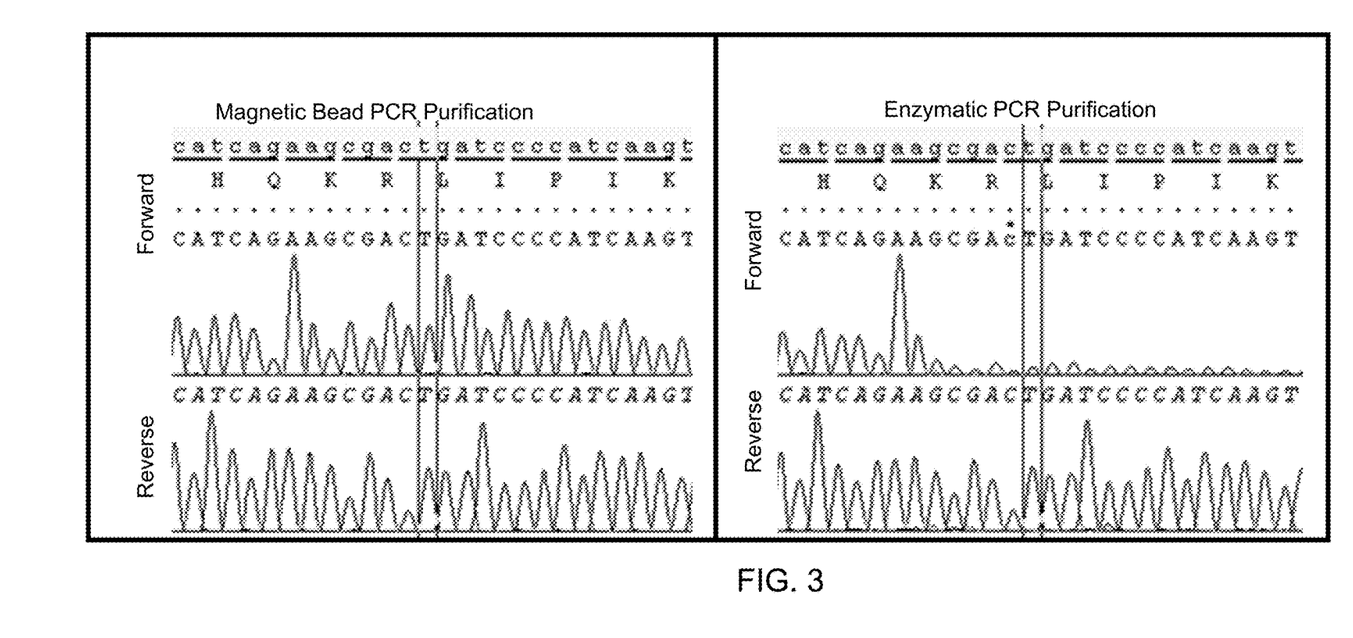
FIG. 3 illustrates a characteristic drop-off in signal intensity seen when enzymatic PCR purification is used instead of magnetic beads. This is likely because enzymatic purification fails to remove LNA prior to bi-directional sequencing.

A characteristic drop-off in signal intensity is often seen if too high a concentration of LNA is used, or if post-PCR purification failed to remove LNA prior to bi-directional sequencing. The impact of the latter is demonstrated when AMpure XP magnetic bead purification (FIG. 3, left panel) is substituted for enzymatic purification (FIG. 3, right panel). Thus, while enzymatic purification may be an attractive option when working with greater sample numbers, it is inappropriate for application to WTB-PCR because it fails to remove LNA from solution prior to sequencing.

Figure 4:
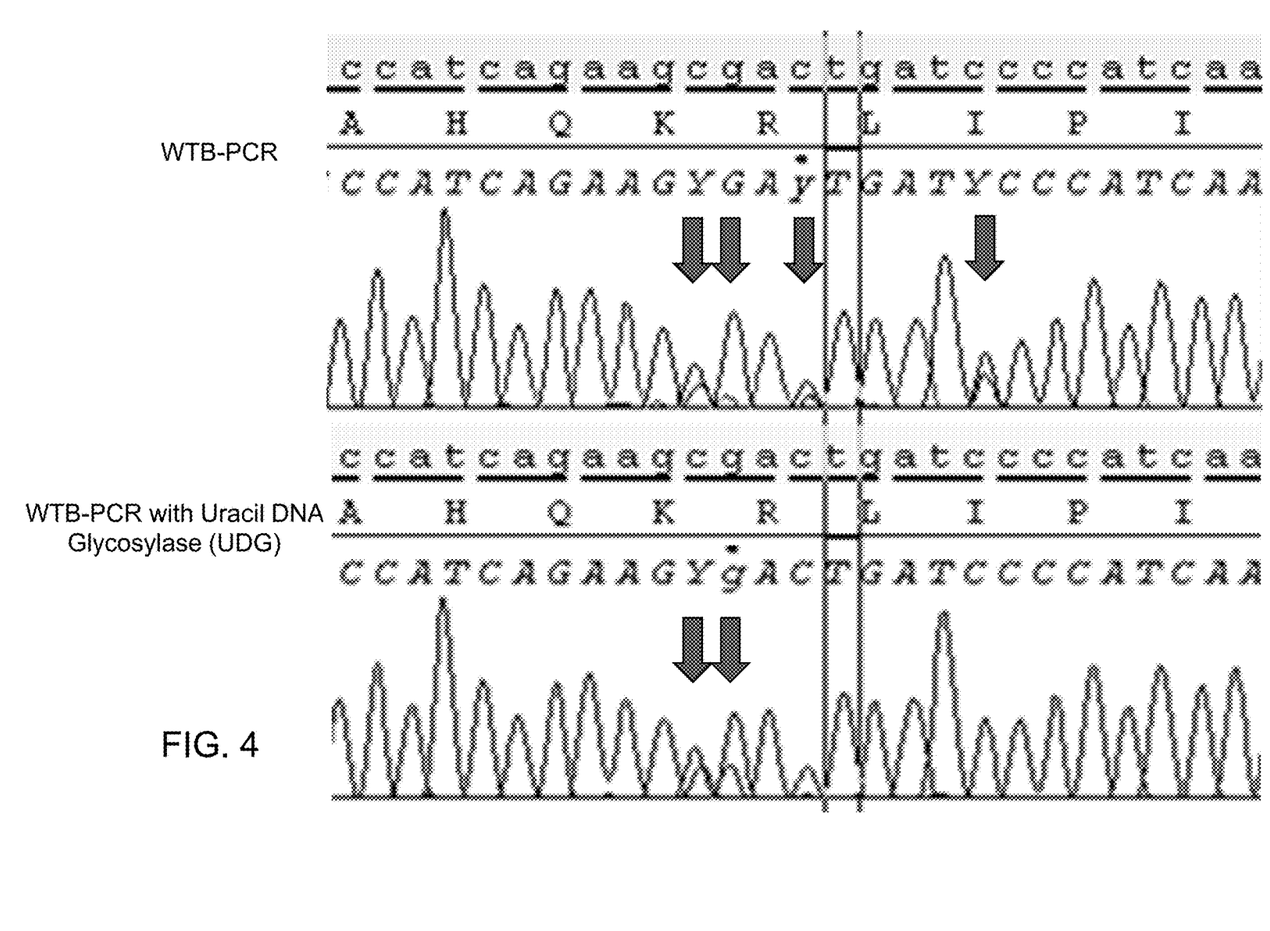
FIG. 4 illustrates that C:G>T:A sequencing artifacts arise in FFPE tissue when cytosine or methylated cytosine are deaminated via formalin fixation to uracil or thymine, respectively. Uracil DNA glycosylase (UDG) can excise uracil prior to WTB-PCR helping to reduce sequencing artifacts. However, thymine resulting from deaminated 5-methylcytosine, which frequently occurs at CpG islands, cannot be excised by UDG. Decreasing the concentration of LNA used in WTB-PCR may help to reduce the occurrence of sequencing artifacts that are not remedied by UDG treatment.

FIG. 4 provided a comparison of the results of WTB-PCT without and with UDG treatment to reduce deamination artifacts. The arrows in FIG. 4 point to examples of sequence artifacts frequently found in FFPE-derived DNA as a result of cytosine deamination (C:G>T:A). While the actual causes of cytosine deamination are poorly understood, any PCR-based assay that enriches for mutant alleles will detect these low frequency artifacts. False positives due to deamination are best avoided by starting with high quality template material. In cases where this is not possible, treatment with uracil DNA glycosylase (UDG) during extraction can aid in limiting the frequency and intensity of deamination artifacts. UDG treatment of FFPE tissue during extraction (as part of the GeneRead DNA FFPE kit) excises deaminated cytosine residues, thereby preventing artificially induced C:G>T:A mutations. (see FIG. 4, lower panel). However, 5-methyl-cytosine residues that frequently occur at CpG dinucleotides are deaminated to thymine, which cannot be excised by UDG, indicated by the arrows in the lower panel of FIG. 4. The resulting sequencing artifacts are fairly recognizable and often appear as tandem mutations. If samples have already been extracted, UDG treatment can be implemented in a secondary extraction with relatively low DNA loss.

Example 2: MYD88 Mutation Detection

Patients and Samples:

Patient material was submitted for MYD88 gene mutation status for various referral reasons. All work was performed with Institutional Review Board (IRB) approval. A total of 153 patient samples were submitted, including fresh bone marrow aspirate (BM), fresh peripheral blood (PB), and formalin-fixed, paraffin-embedded (FFPE) tissues. Routine Flow cytometry data was available on 9/37 retested positive patient samples (PPS) (see Table 4).

DNA Extraction:

Using the QIAcube automated DNA extraction machine and the DNA blood mini kit or FFPE tissue kit (Qiagen; Venlo, Netherlands), we extracted DNA according to manufacturer's instruction. Extracted DNA was then quantified using a Nanodrop 2000 (Thermo Fisher Scientific; Waltham, Mass., U.S.A.) instrument and adjusted to approximately 50-100 ng/uL with $H_2O$.

DNA Sequencing:

153 patient samples were run using WTB-PCR. We randomly selected 37 of the 62 patient samples found to be positive by WTB-PCR and subjected them to both traditional PCR (T-PCR) and WTB-PCR followed by Sanger sequencing. These 37 samples were representative of the 66 positives (see Table 3).

WTB-PCR followed by sequencing was performed on a negative control comprised of tumor-free FFPE colon tissue (N=8), BM/PB (N=3), and thyroid cyst aspirate (TC) (N=1) derived from patients who had no indication of WM, DLBCL, IgM-MGUS, or SMZL. 6 of these samples (5 FFPE and 1 BM)—which were positive for novel mutations—were subjected to treatment with uracil-DNA glycosylase using the GeneRead DNA FFPE kit (Qiagen; Venlo, Netherlands) in order to determine if these novel mutations were artifacts or real.

The MYD88 assay was developed to amplify exon 5 of MYD88 (G259-N291) and 110 nucleotides located in the 5' intronic region in order to cover the splice site and part of the intron. 0.25 uL Fast Start Taq DNA polymerase (Roche; Basel, Switzerland), 2.5 uL PCR reaction buffer 10×w/20 mM MgCl2, 250 uM dNTPs (Invitrogen; Waltham, Mass., U.S.A.), 0.2 uM forward primer (tgt aaa acg acg gcc agt TGC CAG GGG TAC TTA GAT GG), 0.2 uM reverse primer (cag gaa aca gct atg acc GGT TGG TGT AGT CGC AGA CA)(IDT; Coralville, Iowa, U.S.A.), 1.2 uM MYD88LNA (TCAGA+AG+C+G+A+C+T+G+A+T+CC/invdT/) (Exiqon; Vedbaek, Denmark), and 3 uL genomic DNA (50-100 ng/uL) were added to DNAse, RNAse-free, ultra-pure H$_2$O to create a final solution volume of 25 uL/reaction. Both PCR primers were designed with a 5'-M13 sequence (M13-forward: tgt aaa acg acg gcc agt; M13-reverse: cag gaa aca gct atg acc) to allow for annealing of complementary sequencing primers. T-PCR comprised an identical formula lacking only LNA. The LNA oligo was designed to cover amino acids Q262-1266 and featured a 3'-inverted dT to inhibit both extension by DNA polymerase and degradation by 3' exonuclease. Both reactions were subjected to identical thermocycler settings; initial denaturation at 95° C. for 6 minutes; 40 cycles of denaturation at 95° C. for 30 seconds, primer annealing at 56° C. for 30 seconds, and extension at 72° C. for 1 minute 20 seconds; this was followed by a final extension at 72° C. for 10 min. PCR products were enzymatically purified using ExoSAP-IT (Affymetrix; Santa Clara, Calif., U.S.A.) or Agencourt AMPure XP (Beckman Coulter; Brea, Calif., U.S.A.), bi-directionally sequenced using a BigDye Terminator v3.1 Cycle sequencing kit (Life Technologies; Waltham, Mass., U.S.A.), and subjected to ethanol precipitation. The precipitated DNA was then resuspended in 10 uL Hi-Di Formamide (Life Technologies; Waltham, Mass., U.S.A.), denatured at 95° C. for 3', and run on the ABI 3730XL sequencer. Results were analyzed using ABI Prism® SeqScape software and aligned to GenBank Acc# NM_002468.

A serial dilution was completed in order to demonstrate WTB-PCR sensitivity. Genomic DNA taken from a sample that tested positive for MYD88 mutation (L265P) was quantified using a Qubit dsDNA broad range assay kit (Invitrogen; Waltham, Mass., U.S.A.) and diluted to 20 ng DNA per uL with H$_2$O. This DNA was serially diluted with wild-type genomic DNA (also 20 ng/uL).

Resulting Improvement of Sensitivity in Detecting MYD88 Mutations Using WTB-PCR:

Positive selection for mutant alleles by WTB-PCR greatly increased assay sensitivity when compared to T-PCR.

Figure 5:
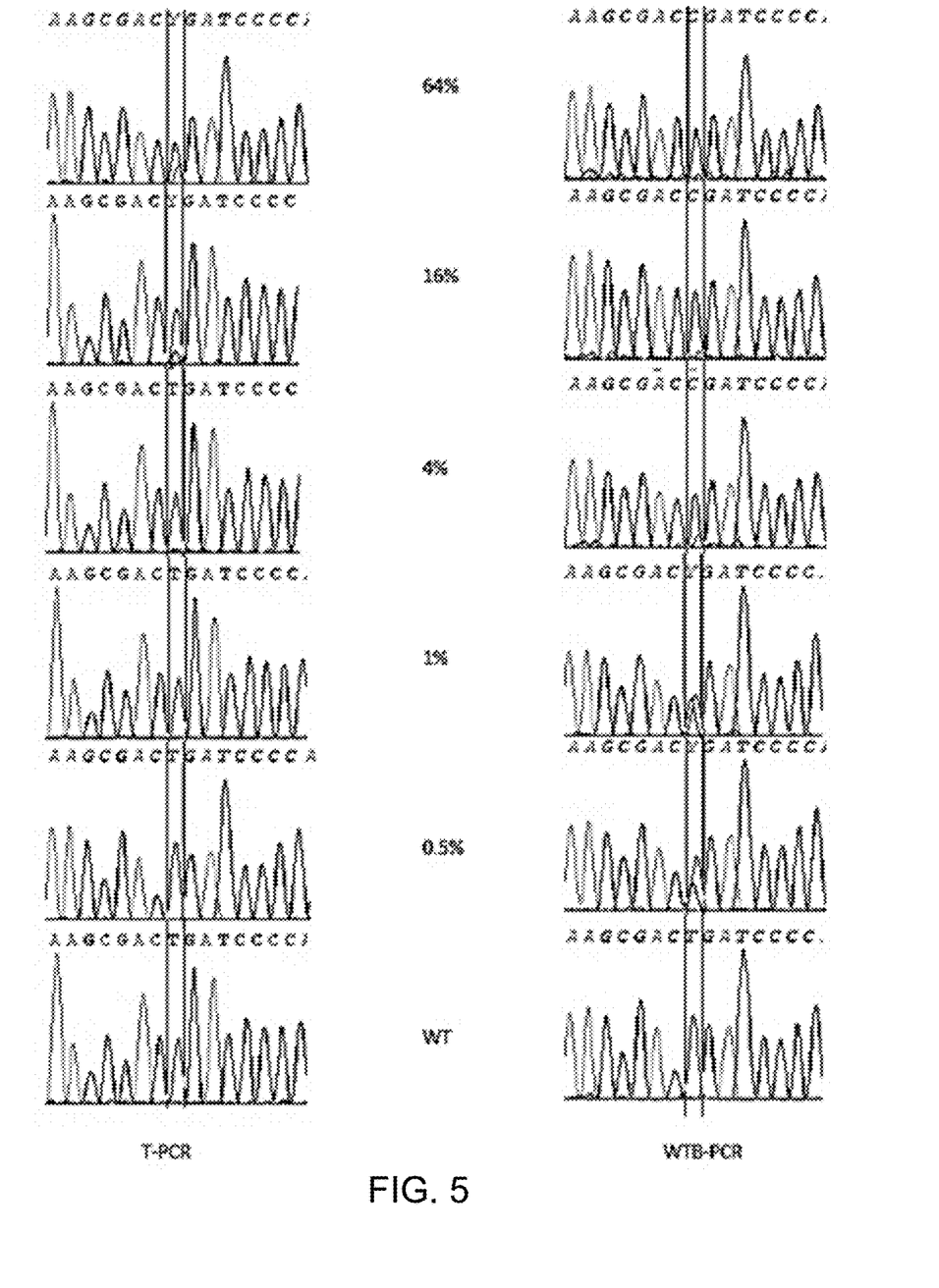
FIG. 5 is a set of chromatograms for DNA sequences comparing conventional T-PCR and WTB-PCR sensitivity. Mutant genomic DNA taken from paraffin embedded lymph nodal tissue. Diluted in 1:1 series with WT genomic DNA taken from peripheral blood.

T-PCR was able to detect up to 16% mutant allele in a background of WT allele, while WTB-PCR was able to detect less than 0.5% (see FIG. 5). Wild-type DNA was negative for mutations by both T-PCR and WTB-PCR, demonstrating assay specificity Agencourt AMPure XP post-PCR purification yielded far cleaner Sequencing chromatograms than ExoSAP-IT purification and is therefore the preferred methodology (Data not shown).

Higher Rate of Detection in Clinical Samples Using WTB-PCR:

Using WTB-PCR, MYD88 mutations were detected in 62/153 samples (40.5%), including 58/153 L265P (94% of mutations) and 4/153 R264* (6% of mutations) (see Table 3).

Table 3 provides a listing of samples tested by routine lab with WTB-PCR and randomly selected positive patient samples tested with both WTB-PCR and T-PCR, where WTB-PCR means wild-type blocking PCR, T-PCR means traditional PCR, and N/A means not applicable.

TABLE 3

|  | WTB-PCR | T-PCR |
|---|---|---|
| All samples N = 153 | 62 (40.5%) | N/A |
| L265P | 58 (94%) | N/A |
| R264* | 4 (6%) | N/A |
| Samples tested by both N = 37 | 37 | 13 |
| False negatives (%) | 0 | 65 |
| L265P | 34 | 13 |
| R264* | 2 | 0 |
| 789g>a (synonymous) | 1 | 0 |

Thirty-seven (37) of the randomly selected patient samples with known mutated MYD88 were subjected to T-PCR without LNA; followed by sequencing. Using this conventional approach, of the 37, only 13 revealed MYD88 mutations (35%), as indicated in Tables 3 and 4. Thus, routine testing using traditional PCR only yielded a false negative report rate of 65%. Parallel repeat testing of 37 positive samples with WTB-PCR yielded zero false negatives. WTB-PCR additionally revealed a novel synonymous mutation (793c>t) present in 3/37 positive patient samples (PPS), all of which were concurrent with either R264* or L265P mutations. One additional novel synonymous mutation 789g>a was discovered by WTB-PCR.

Table 4 below provides a listing of positive patient samples ("PPS") tested by WTB-PCR and T-PCR.

TABLE 4

| Sample | Age | Gender | PPS (T-PCR w/o LNA) | PPS (WTB-PCR w/LNA) | Source | Comment |
|---|---|---|---|---|---|---|
| 1 | 83 | F | unmutated | 794t>c (L265P) | BM | 2-3% CLL cells by Flow |
| 2 | 57 | F | unmutated | 794t>c (L265P) | BM | |
| 3 | 68 | F | unmutated | 794t>c (L265P) | BM | 3% Lymphoplasma cytoid by Flow |
| 4 | 77 | F | unmutated | 794t>c (L265P) | BM | |
| 5 | 73 | M | 794t>c (L265P) | 794t>c (L265P) | BM | |
| 6 | 83 | F | Unmutated | 790c>t (R264*), 793c>t(silent) | PB | 46% Mantle Cells, confirmed by FISH |
| 7 | 73 | M | Unmutated | 794t>c (L265P) | PB | |
| 8 | 60 | F | 794t>c (L265P) | 794t>c (L265P) | Paraffin | |
| 9 | 85 | F | Unmutated | 794t>c (L265P) | BM | |
| 10 | 68 | M | 794t>c (L265P) | 794t>c (L265P) | BM | |
| 11 | 61 | M | 794t>c (L265P) | 794t>c (L265P) | Paraffin | |
| 12 | 67 | M | Unmutated | 794t>c (L265P) | Paraffin, BM | 60% Plasmacytoid cells by bone marrow biopsy, but 4% by Flow |

TABLE 4-continued

| Sample | Age | Gender | PPS (T-PCR w/o LNA) | PPS (WTB-PCR w/LNA) | Source | Comment |
|---|---|---|---|---|---|---|
| 13 | 54 | M | Unmutated | 790c>t (R264*), 793c>t(silent) | BM | 2% MGUS by Flow |
| 14 | 75 | M | Unmutated | 794t>c (L265P), 793c>t(silent) | BM | 3% Lymphoplasmacytoid by Flow |
| 15 | 78 | F | 794t>c (L265P) | 794t>c (L265P) | Paraffin | |
| 16 | 74 | F | Unmutated | 794t>c (L265P) | PB | |
| 17 | 77 | F | 794t>c (L265P) | 794t>c (L265P) | BM | |
| 18 | 69 | M | 794t>c (L265P) | 794t>c (L265P) | BM | |
| 19 | 48 | M | 794t>c (L265P) | 794t>c (L265P) | Paraffin | |
| 20 | 69 | M | 794t>c (L265P) | 794t>c (L265P) | BM | |
| 21 | 74 | M | Unmutated | 794t>c (L265P) | BM | 11% Lymphoplasmacytoid by Flow |
| 22 | 70 | M | Unmutated | 794t>c (L265P) | PB | |
| 23 | 76 | M | 794t>c (L265P) | 794t>c (L265P) | Paraffin | |
| 24 | 65 | M | Unmutated | 794t>c (L265P) | BM | |
| 25 | 42 | M | Unmutated | 794t>c (L265P) | Paraffin | |
| 26 | 75 | F | Unmutated | 794t>c (L265P) | BM | |
| 27 | 65 | F | 794t>c (L265P) | 794t>c (L265P) | Paraffin | |
| 28 | 63 | F | Unmutated | 794t>c (L265P) | BM | |
| 29 | 59 | F | Unmutated | 794t>c (L265P) | BM | |
| 30 | 74 | M | 794t>c (L265P) | 794t>c (L265P) | BM | |
| 31 | 76 | M | Unmutated | 794t>c (L265P) | BM | |
| 32 | 87 | M | Unmutated | 794t>c (L265P) | BM | |
| 33 | 71 | M | Unmutated | 794t>c (L265P) | BM | |
| 34 | 75 | M | 794t>c (L265P) | 794t>c (L265P) | BM | 40% Lymphoplasmacytoid by Flow |
| 35 | 83 | M | Unmutated | 794t>c (L265P) | BM | 2% Lymphoplasmacytoid by Flow |
| 36 | 82 | M | Unmutated | 794t>c (L265P) | Paraffin | |
| 37 | 81 | M | Unmutated | 789g>a (silent) | BM | |

Median abnormal neoplastic cells (determined by routine lab flow cytometry data) for samples where mutation was detected by WTB-PCR but not T-PCR was 3% (N=7 range=2-11%) (see Table 4). One outlier, sample 6—with 46% mantle cell lymphoma cells (confirmed by FISH and flow cytometry data) and a R265*, 793c>t dual mutation—was detected by WTB-PCR but not T-PCR (see Table 4). This likely represented the presence of the mutation in a subclone of the lymphoma cells and a transformation to DLBCL, ABC subtype.

Figure 6A:
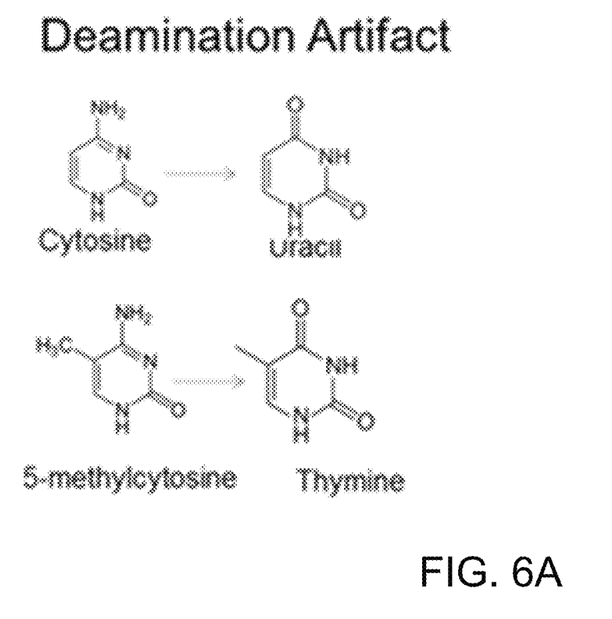
FIG. 6A is a diagram showing deamination artifacts associated with high sensitivity MYD88 mutation detection using WTB-PCR/sequencing and comparing the use of UDG for reducing these artifacts. CpG islands at R264* remains resistant to UDG due to conversion to Thymine rather than Uracil upon deamination.
Figure 6B:
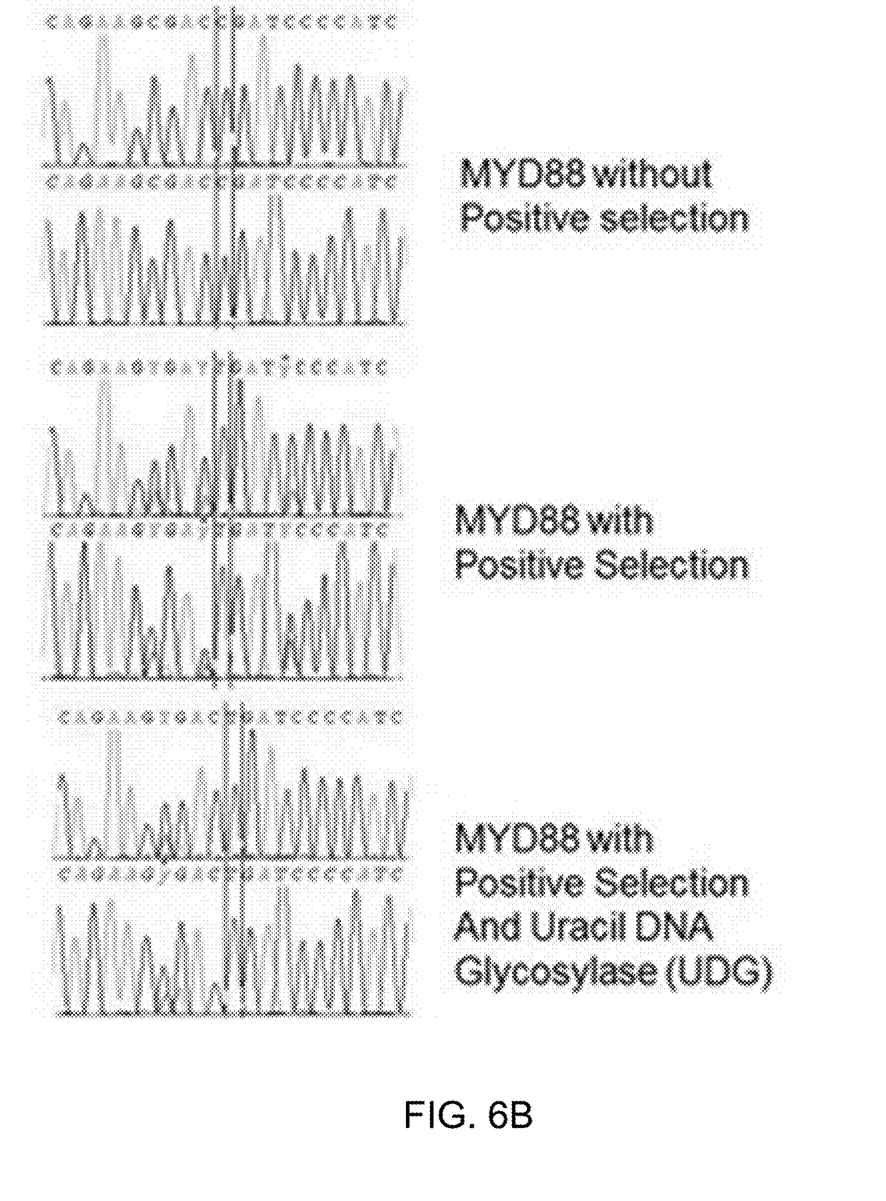
FIG. 6B is a comparison of the effect of Uracil-DNA Glycosylase (UDG) treatment without and with positive selection.

Novel mutations, including R264*, 793c>t, and 798c>t, were detected in 7/8 of normal FFPE colon tissue samples and 3/12 in BM/PB/TC samples. No L265P mutations were detected. Sequence artifacts occurred as a result of cytosine deamination, as shown in FIG. 6A. Uracil-DNA Glycosylase (UDG) treatment greatly reduced all sequence artifacts with the exception of R264* mutations (see FIG. 6B). All samples indicating novel C:G>T:A mutations from FFPE have been omitted from the mutation rate calculations because, based on this data, they were most likely artifacts. The remaining novel mutations are from PB, BM, or TC and were not omitted due to the fact that there was no evidence of induced sequence artifacts in unfixed material.

Given the 65% false negative report rate, WTB-PCR is clearly a superior methodology for detecting MYD88 mutations than T-PCR in random clinical testing when Sanger sequencing is used. Additionally, reproducibility within the technique (see Table 4) demonstrates the assay's accuracy. Routine lab flow data on patient material indicates that low percentages of abnormal neoplastic cells are likely the reason for the inability to detect MYD88 mutations in the majority of false negatives by T-PCR (median abnormal cellularity is 3%). Given sensitivity levels of Sanger sequencing following T-PCR (16% mutant allele in a background of WT allele), this low level abnormal population possessing MYD88 mutations would not be detected, except by WTB-PCR. The identification of MYD88 mutation in the exceptional mantle cell sample by WTB-PCR but not T-PCR indicates that only a sub-clonal population is positive for the MYD88 mutation. The benefit of using WTB-PCR over AS-PCR is clearly evident in the mutation frequency of R264* and discovery of two novel synonymous substitutions (793c>t and 798g>a). Using WTB-PCR, R264* in particular was discovered in 6% of samples found positive for MYD88 mutations. This new rate of observation warrants further investigation into the functional effect of this specific type of mutation.

Sequence artifacts are frequently found in FFPE-derived DNA as a result of cytosine deamination (C:G>T:A). Though the actual causes of cytosine deamination are poorly understood, any assay that greatly increases sensitivity (Next-generation sequencing or AS-PCR) will detect these low frequency artifacts. The high rate of novel mutations detected in normal FFPE tissue indicates that WTB-PCR is amplifying template DNA with these artifacts. In order to reduce the number of artifact-induced false positives but retain true mutations, we treated FFPE DNA with UDG prior to WTB-PCR. It has been demonstrated that this treatment markedly reduces sequence artifacts found in FFPE DNA while retaining true mutations. In our assay, this resulted in reduction of all alternate mutations with the exception of R264* mutations (see FIG. 6B). We concluded that R264* mutations, which occur at a CpG dinucleotide, involve methylated cytosine, which is deaminated to thymine rather than uracil and, therefore, cannot be removed by UDG. CpG dinucleotides are sites of frequent mutation in the human genome as a result of the modification of the 5' cytosine by cellular DNA methyltransferases and the consequent high frequency of spontaneous deamination of 5-methyl cytosine (5 mC) to thymine. Since the same R264* mutations were detected in fresh BM and PB, we also concluded that these are in fact very low frequency spontaneous deamination events that should not be considered artifacts as a result of formalin fixation. It is, however, difficult to discern the difference between artifacts and real mutations in FFPE; for this reason, we have omitted all novel mutations in FFPE-derived DNA from our results. When performing assays with high sensitivity (e.g., NGS or AS-PCR), an extraction methodology incorporating UDG treatment is highly recommended but is not entirely sufficient at removing artifactual DNA.

Positive selection by WTB-PCR has demonstrated its ability to uncover low frequency and novel mutations. Additional assays can also be developed to explore more accurate mutation rates of other low frequency mutations that occur on other exons. These include L103 and Q143 mutations, which have been reported in primary central nervous system lymphoma. Accurate detection of abnormal neoplastic lymphocytes in bone marrow or paraffin-embedded tissue can be difficult. Therefore, establishing a system for the enrichment of mutations is invaluable in clinical testing.

Given the diagnostic, prognostic, and therapeutic purposes of MYD88 mutation testing, the need for an accurate, high sensitivity assay—capable of being run in large volume—is a necessity. Using WTB-PCR with Sanger sequencing has multiple advantages in the clinical setting. Unlike allele-specific testing, WTB-PCR/Sanger testing allows the detection of undiscovered mutations and also provides adequate internal controls for ruling out false positives. In conclusion, WTB-PCR with LNA followed by sequencing provides a high sensitivity assay with several advantages over other methods currently offered (AS-PCR). Its additional utility in revealing low percentage mutant populations—most notably unexpected mutation types (R264*, 793c>t)—is invaluable and will guide future research.

As previously noted, the examples described herein employing LNA blocking and Sanger sequencing are not intended to be limiting. Rather, the approach using wild-type blocking nucleotides to selectively amplify low-occurrence MYD88 mutations to enhance the sensitivity for such mutations may be achieved using the general principles described herein in conjunction with other artificial nucleotides (e.g., BNA, PNA, XNA, etc.) and using other sequencing techniques as are known in the art, including, but not limited to to next generation sequencing (NGS), polymerase chain reaction (PCR), pyrosequencing, dye sequencing, sequencing by synthesis, and ion semiconductor sequencing, and others.

REFERENCES (INCORPORATED HEREIN BY REFERENCE)

1.) Watters T M, Kenny E F, O'Neill L A: Structure, function and regulation of the Toll/IL-1 receptor adaptor proteins. *Immunol Cell Biol* 2007, 85(6): 411-419.
2.) Loiarro M, Gallo G, Fantò N, De Santis R, Carminati P, Ruggiero V, Sette C: Identification of critical residues of the MyD88 death domain involved in the recruitment of downstream kinases. *J Biol Chem* 2009, 284(41): 28093-28103.
3.) Treon S P, Xu L, Yang G, Zhou Y, Liu X, Cao Y, Hunter Z R: MYD88 L265P somatic mutation in Waldenström's macroglobulinemia. *N Engl J Med* 2012, 367(9): 826-833.
4.) Ngo V N, Young R M, Schmitz R, Jhavar S, Xiao W, Lim K H, Staudt L M: Oncogenically active MYD88 mutations in human lymphoma. *Nature* 2011, 470(7332): 115-119.
5.) Varettoni M, Arcaini L, Zibellini S, Boveri E, Rattotti S, Riboni R, Cazzola M: Prevalence and clinical significance of the MYD88 (L265P) somatic mutation in Waldenström's macroglobulinemia and related lymphoid neoplasms. *Blood* 2013, 121(13): 2522-2528.
6.) Salar A, Garcia-Pallarols F, Fernández-Rodríguez C, Sánchez-González B, Carmen Vela M: 1690 MYD88 (L265P) Mutation Confers Very Poor Response and Outcome after Second-Line Therapy in Patients with Diffuse Large B-Cell Lymphoma (DLBCL). Presentation at 56th American Society of Hematology Meeting and Exposition, San Francisco, Calif., 2014.
7.) Pasqualucci L, Trifonov V, Fabbri G, Ma J, Rossi D, Chiarenza A, Dalla-Favera R: Analysis of the coding genome of diffuse large B-cell lymphoma. *Nat Genet* 2011, 43(9): 830-837.
8.) Wang D, Jiang W, Sullivan T, Bhagat L: 508 Novel Approach to the Potential Treatment of Patients with B-Cell Lymphomas Harboring the MYD88 L265P Mutation: Combination Treatment with TLR Antagonist and Rituximab. Presentation at 56th American Society of Hematology Meeting and Exposition, San Francisco, Calif., 2014.
9.) Xu L, Hunter Z R, Yang G, Zhou Y, Cao Y, Liu X, . . . Treon S P: MYD88 L265P in Waldenström macroglobulinemia, immunoglobulin M monoclonal gammopathy, and other B-cell lymphoproliferative disorders using conventional and quantitative allele-specific polymerase chain reaction. *Blood* 2013, 121(11): 2051-2058.
10.) Gertz, M A: Waldenström macroglobulinemia: 2012 update on diagnosis, risk stratification, and management. *Am J Hematol* 2012, 87(5): 503-510.
11.) Wang J Q, Jeelall Y S, Horikawa K: Emerging targets in human lymphoma: targeting the MYD88 mutation. *Blood & Lymphatic Cancer: Targets & Therapy* 2013, 3: 53-61.
12.) Dominguez P L, Kolodney M S: Wild-type blocking polymerase chain reaction for detection of single nucleotide minority mutations from clinical specimens. *Oncogene* 2005, 24(45), 6830-6834.
13.) Quach, N, Goodman, M F, Shibata, D: In vitro mutation artifacts after formalin fixation and error prone translesion synthesis during PCR. *BMC clinical pathology* 2004, 4(1): doi:10.1186/1472-6890-4-1
14.) Gallegos Ruiz M I, Floor K, Rijmen F, Grünberg K, Rodriguez J A, Giaccone G: EGFR and K-ras mutation analysis in non-small cell lung cancer: comparison of paraffin embedded versus frozen specimens. *Cell Oncol* 2007, 29(3): 257-264.
15.) Solassol J, Ramos J, Crapez E, Saifi M, Mangé A, Vianès E, Maudelonde T: KRAS mutation detection in paired Frozen and Formalin-Fixed Paraffin-Embedded (FFPE) colorectal cancer tissues. *Int J Mol Sci* 2011, 12(5): 3191-3204.
16.) Yost S E, Smith E N, Schwab R B, Bao L, Jung H, Wang X, Voest E, Pierce J P, Messer K, Parker B A, Harismendy O, Frazer K A: Identification of high-confidence somatic mutations in whole genome sequence of formalin-fixed breast cancer specimens. *Nucleic Acids Res* 2012, 40 (14): doi:10.1093/nar/gks299
17.) Do H, Wong S Q, Li J, Dobrovic A: Reducing sequence artifacts in amplicon-based massively parallel sequencing of formalin-fixed paraffin-embedded DNA by enzymatic depletion of uracil-containing templates. *Clin Chem* 2013, 59(9), 1376-1383.
18.) Do H, Dobrovic A: Dramatic reduction of sequence artefacts from DNA isolated from formalin-fixed cancer biopsies by treatment with uracil-DNA glycosylase. *Oncotarget* 2012, 3(5): 546-558.
19.) Cooper D N, Krawczak M: Cytosine methylation and the fate of CpG dinucleotides in vertebrate genomes. *Hum Genet* 1989, 83(2): 181-188.
20.) Adams R L P, Eason R: Increased G+C content of DNA stabilises methyl CpG dinucieotides. *Nucl Acids Res* 1984, 12(14): 5869-5877.
21.) Adams R L, Davis T, Rinaldi A, Eason R: CpG deficiency, dinucleotide distributions and nucleosome positioning. *Eur Biochem* 1987, 165(1): 107-115.
22.) Trøen G, Warsame A, Delabie J: CD79B and MYD88 Mutations in Splenic Marginal Zone Lymphoma. *ISRN Oncology*, 2013, 252318. doi: 10.1155/2013/252318
23.) Goymer P: Synonymous mutations break their silence. *Nature Reviews Genetics* 2007, 8(2): 92-92.
24.) Gonzalez-Aguilar A, Idbaih A, Boisselier B, Habbita N, Rossetto M, Laurenge A, Hoang-Xuan K: Recurrent mutations of MYD88 and TBL1XR1 in primary central nervous system lymphomas. *Clin Cancer Res* 2012, 18(19): 5203-5211.

The invention claimed is:

1. A method for detecting MYD88 mutations in a patient sample, the method comprising:
   isolating DNA from a sampling bone marrow aspirate (BM), fresh peripheral blood (PB), and formalin-fixed, paraffin-embedded (FFPE) tissues sample obtained from a patient suspected of having a condition associated with MYD88 mutations;
   performing PCR on the extracted DNA to produce amplified DNA while blocking amplification of wild-type DNA with an LNA oligonucleotide comprising SEQ ID NO. 5;
   sequencing the amplified DNA in an automated sequencer;
   analyzing an output of the automated sequencer to identify MYD88 mutations in the sequence.

2. The method of claim 1, further comprising, prior to sequencing, applying a uracil DNA-glycosylase treatment to the sample to remove sequence artifacts.

3. The method of claim 1, wherein the amplification is performed with the following primers comprising SEQ ID NO. 1 and SEQ ID No. 2.

4. The method of claim 1, wherein the step of sequencing is performed using a sequencing method selected from the group consisting of Sanger sequencing, next generation sequencing, polymerase chain reaction, pyrosequencing, dye sequencing, sequencing by synthesis, and ion semiconductor sequencing.

5. The method of claim 1, wherein the MYD88 mutation is associated with a cancer is selected from the group consisting of Waldenström's Macroglobulinemia (WM), diffuse large B-Cell lymphoma (DLBCL), monoclonal gammopathy of unknown significance (MGUS), and splenic marginal zone lymphoma (SMZL).

6. A method for analyzing a patient sample for presence or absence of MYD88-associated cancer, the method comprising:
   extracting DNA from one or more samples obtained from a patient suspected of having a condition associated with MYD88 mutations;
   performing PCR on the extracted DNA to produce amplified DNA while blocking amplification of wild-type DNA using an LNA oligonucleotide with SEQ ID NO. 5, wherein amplification is performed with primers comprising SEQ ID NO. 1 and SEQ ID NO. 2;
   sequencing the amplified DNA in an automated sequencer; and
   analyzing an output of the automated sequencer to identify MYD88 mutations in the sequence.

7. The method of claim 6, wherein the one or more samples comprise bone marrow aspirate (BM), fresh peripheral blood (PB), and formalin-fixed, paraffin-embedded (FFPE) tissues.

8. The method of claim 6, further comprising, prior to sequencing, applying a uracil DNA-glycosylase treatment to the one or more samples to remove sequence artifacts.

9. The method of claim 6, wherein the MYD88-associated cancer is selected from the group consisting of Waldenström's Macroglobulinemia (WM), diffuse large B-Cell lymphoma (DLBCL), monoclonal gammopathy of unknown significance (MGUS), and splenic marginal zone lymphoma (SMZL).

\* \* \* \* \*